(12) United States Patent
Oh

(10) Patent No.: US 7,008,222 B2
(45) Date of Patent: Mar. 7, 2006

(54) ROOT CANAL PLUGGING APPARATUS FOR DENTAL WORK

(76) Inventor: Suk Song Oh, 358-5 Sjikdong, Dukhoi APT 213 Ho, Hungdukgu, Chungjushi, Choongchungbukdo, 361-102 (KR)

( * ) Notice: Subject to any disclaimer, the term of this patent is extended or adjusted under 35 U.S.C. 154(b) by 76 days.

(21) Appl. No.: 10/601,522

(22) Filed: Jun. 24, 2003

(65) Prior Publication Data

US 2004/0265772 A1    Dec. 30, 2004

(51) Int. Cl.
*A61C 5/02*    (2006.01)

(52) U.S. Cl. .................. 433/81; 433/224; 433/32

(58) Field of Classification Search ............ 433/81, 433/83, 224, 102, 32, 89
See application file for complete search history.

(56) References Cited

U.S. PATENT DOCUMENTS

| | | | |
|---|---|---|---|
| 4,265,618 A | | 5/1981 | Herskovitz et al. ............ 433/32 |
| 4,357,136 A | | 11/1982 | Herskovitz et al. ......... 433/224 |
| 4,392,827 A | | 7/1983 | Martin ........................ 433/32 |
| 4,441,013 A | | 4/1984 | Masreliez .................... 219/231 |
| 4,527,560 A | | 7/1985 | Masreliez ................. 128/303.1 |
| 4,992,045 A | | 2/1991 | Beisel ......................... 433/32 |
| 5,017,137 A | * | 5/1991 | Weissman ................... 433/102 |
| 5,043,560 A | | 8/1991 | Masreliez ................... 219/497 |
| 5,807,261 A | * | 9/1998 | Benaron et al. ............ 600/473 |
| 5,893,713 A | | 4/1999 | Garman et al. ............... 433/32 |
| 5,921,775 A | | 7/1999 | Buchanan .................... 433/102 |
| 5,934,903 A | | 8/1999 | Marlin ........................ 433/81 |
| 6,168,432 B1 | | 1/2001 | Marlin ........................ 433/81 |
| 6,270,343 B1 | | 8/2001 | Martin ........................ 433/32 |
| 6,416,320 B1 | * | 7/2002 | Roffe et al. .................. 433/32 |
| 6,701,189 B1 | | 3/2004 | Fang et al. |
| 2002/0086264 A1 | * | 7/2002 | Okawa et al. ............... 433/89 |

FOREIGN PATENT DOCUMENTS

WO    WO 01/49202    7/2001

* cited by examiner

*Primary Examiner*—Cary E. O'Connor
*Assistant Examiner*—Candice C. Stokes
(74) *Attorney, Agent, or Firm*—Park Law Firm; John K. Park

(57) ABSTRACT

A root canal plugging apparatus for dental work is provided. The apparatus includes a pen tip for compacting a filler material in a root canal, a pen for holding the pen tip, a tapered needle for injecting the filler material into the root canal, and a gun for holding the needle. The pen tip is electrically connected to the pen. The pen tip has a hollow body, a heating element, and a temperature sensor. The body has a first end and a second end. The first end is attached to the pen, and the second end is inserted into the root canal. The heating element is positioned inside the body at a predetermined distance from the second end, and the temperature sensor is positioned inside the body. The temperature sensor measures the temperature at the second end.

4 Claims, 5 Drawing Sheets

ROOT CANAL PLUGGING APPARATUS FOR DENTAL WORK

BACKGROUND OF THE INVENTION

The present invention relates, in general, to a root canal plugging apparatus for dental work and, more particularly, to a complex root canal plugging apparatus consisting of a controller, a gun-type injection device, and a pen-type vertical spreader. The invention provides improvements in the pen-type vertical spreader and in the gun-type injection device.

Root canal plugging is the last procedure of treating and curing processes for the root canal, and one of the essential processes.

During a dental treatment for a decayed tooth in a dental clinic, a dentist appropriately removes decayed parts from the tooth using dental drills, reamers, files and burs, and performs a root canal plugging procedure for packing a root canal with a filler material, prior to covering the tooth packed with the filler material using a crown.

Typically, Gutta-Percha cones have been preferably used as such filler materials during the root canal plugging procedures. The Gutta-Percha is the milky juice of Malaysian trees of the sapodilla family, especially Palaguium or Payena trees, and has a semisolid phase at a normal temperature, but becomes a hard rubberlike gum when being compressed or heated. The Gutta-Percha in the form of such a hard rubberlike gum is so-called "white Gutta-Percha". The dentally usable Gutta-Percha cones are produced by adding zinc oxide, barium sulfate, wax and pigment to the Gutta-Percha, and kneading them in a mixer prior to extruding the mixture in the form of a sheet using a roll. The sheet type extruded mixture is, thereafter, cut into pieces, and the pieces are shaped into cones to form desired Gutta-Percha cones having different sizes. The Gutta-Percha cones have been most widely used as the root canal filler materials since they are biologically compatible with living bodies and not harmful to the root apexes of human teeth.

A key point of the root canal plugging procedure is to plug the root canal tightly with Gutta-Percha cones so that there is no dead space in the root canal. The root canal is pretreated prior to plugging. The pretreatment of the root canal is performed by removing infection sources and other decayed materials from the root canal with a drilling device and a cleaning liquid, and forming the root canal to facilitate root canal plugging. The sizes of the Gutta-Percha cones were devised to be same as those of the root canal plugging devices so that plugging might be completed within short time. However, root canals have a very complex shape. The root canal may be curved. There are many root canals that have several branch root canal in addition to a main root canal. It is very hard to completely plug such root canals with Gutta-Percha cones. Since solid Gutta-Percha cones do not have fluidity, although they are useful in plugging the main root canal, it is not possible to use them in plugging the branch root canals.

"Plugging method with heat-softened Gutta-Percha" first introduced by Shilder on 1967 was welcomed by many experts. Various revisions of the plugging method with heat-softened Gutta Percha have been introduced. Even though they have some distadvantages, they are used widely in the clinic.

U.S. Pat. No. 4,265,618 by J. Marlin discloses a root canal plugging method in which a Gutta-Percha cone is inserted into a gun type injection device; the cone is softened; the softened Gutta-Percha is flowed into a root canal through a needle that is installed at the front part of the gun type device; the softened Gutta-Percha is vertically pressed by a plugger, etc. until it is hardened. The method has a disadvantage that not like the case of a solid Gutta-Percha cone, it is difficult to adjust the operating length. Specifically, softened Gutta Percha flows out of the Apicalforamen, resulting in pain of a patient.

U.S. Pat. No. 5,934,903 by J. Marlin discloses a needle for a gun type injection device. The front part of the gun type injection device, through which a plugging material is ejected, has a flange, and a needle, which has two different diameters along its length, is attached to the gun type injection device with a needle hub. While softened Gutta Percha flows smoothly since the needle was made of silver which has good heat conductivity, the needle tends to fracture in a procedure of bending and unbending the needle.

U.S. Pat. No. 4,527,560 by J. Masreliez discloses that a solid Gutta-Percha cone is adjusted to required operation length; a tip that is electrically heated is installed on a probe for dental or medical use; heating is performed at the end of the tip, and the tip is inserted into a root canal; and a Gutta-Percha cone is softened and plugs the root canal. The tip was made of stainless steel and was not elastic. Thus, it was not effective for plugging a curved root canal. Also Masreliez's invention has a disadvantage that it takes a long time to plug a root canal in the clinic.

U.S. Pat. No. 5,893,713 by Gary Garman et al. discloses a tip that is made of super-elastic material. However, it still had the problem of long plugging operation time.

Heating stability is essential for a plugging device in which a tip is connected to a probe and heated electrically. According to in-vitro tests with electrically heated tips, when an apparatus remain heated within a tooth for an extended time, damage may be caused in a certain tissue. It is desirable to minimize heating the root canal apex to avoid such damage. Thus, there has been a need to develop a root canal plugging device having improved controllability.

SUMMARY OF THE INVENTION

The present invention contrives to solve the disadvantages of prior art.

Therefore, an object of the invention is to provide a root canal plugging device that can precisely control the temperature of a tip that heats Gutta-Percha cones.

Another object of the invention is to provide a root canal plugging device that minimizes heating in order to prevent damage to human tissues.

Still another object of the invention is to provide a root canal plugging device that enables convenient installation of a needle to a gun, and prevents fracture of the needle.

To achieve the above-described objects, the invention provides a root canal plugging apparatus for dental work. The apparatus plugs a root canal by filling the root canal with a filler material. The apparatus includes pen tip for compacting the filler material in the root canal, and a pen for holding the pen tip. The pen tip is electrically connected to the pen, and the pen tip has a hollow body, a heating element, and a temperature sensor. The body has a first end and a second end, and the first end is attached to the pen, and the second end is inserted into the root canal. The heating element is positioned inside the body in a way that heat is generated at a predetermined distance from the second end, and the temperature sensor is positioned inside the body. The predetermined distance is in a range from about two (2) mm to three (3) mm. The temperature sensor measures the temperature at the second end.

The pen tip further includes a first conductive wire, a second conductive wire, and an insulation layer. The first conductive wire is electrically connected with the heating element and extends toward the first end of the pen tip. The second conductive wire electrically connects the heating element and the second end of the pen tip. The insulation layer insulates the first conductive wire from the body.

The body is made of stainless steel, and the conductive wires are made of silver. The heating element is made of Chromel, an Ni—Cr alloy, and the insulation layer is made of polyimide.

The pen tip is tapered toward the second end. The heating element forms a K-type temperature sensor.

The apparatus further comprises a needle for injecting the filler material into the root canal, and a gun for holding the needle.

The needle has a cap and a needle portion fixed to the cap. The cap is detachably attached to the gun, and has a knurled portion for preventing slipping.

The needle portion has a shape of taper, and the size of the taper is in a range from about 2/100 to about 6/100.

The advantages of the present invention are numerous in that: (1) the temperature of the pen tip can be precisely controlled in order to avoid discomfort or injury to a patient; (2) positioning of heating element inside the pen tip is optimized to enhance compacting effect; and (3) the needle is easy and convenient to assemble and use.

Although the present invention is briefly summarized, the fuller understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE PREFERRED EMBODIMENTS

Figure 1:
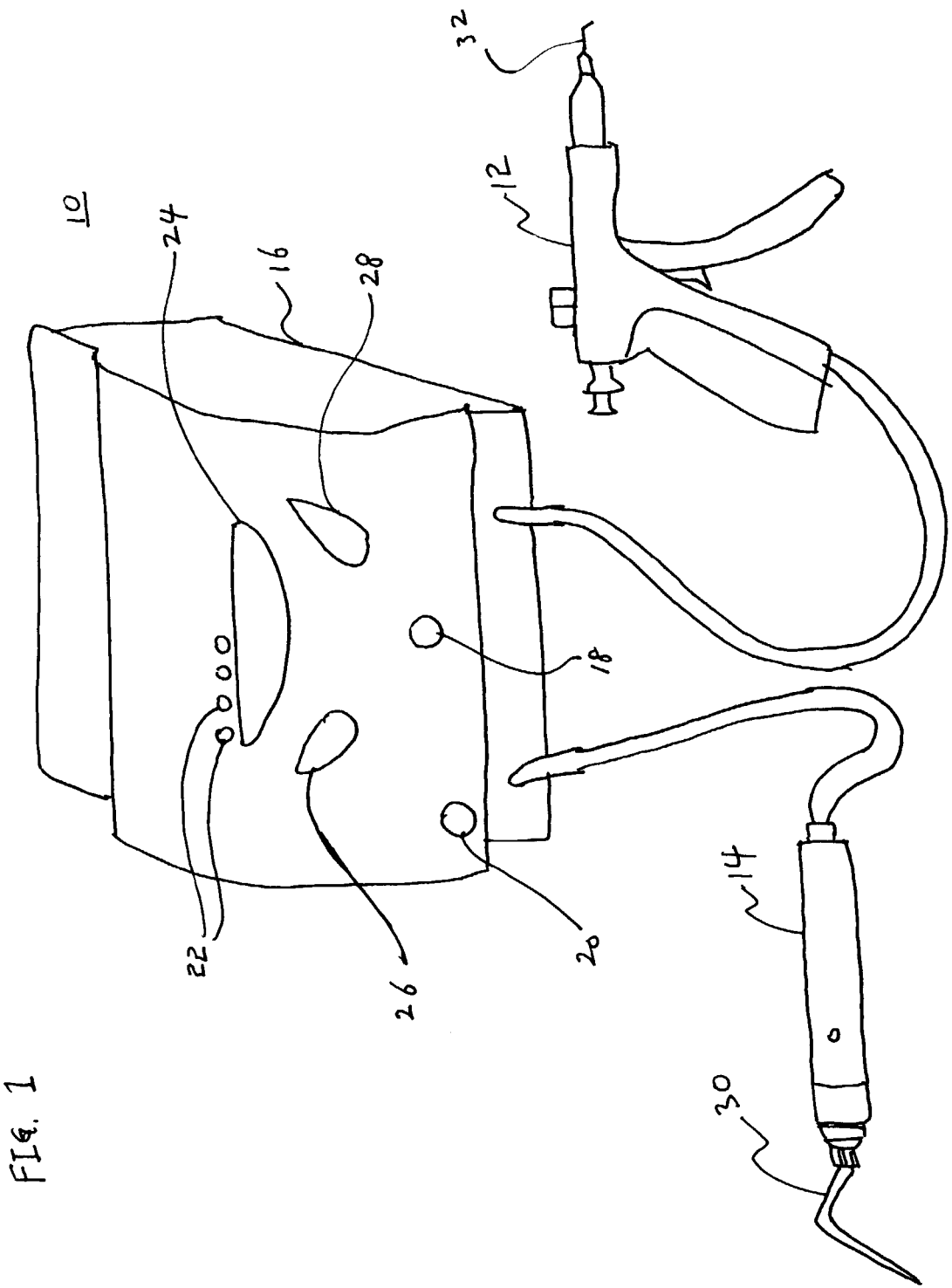
FIG. 1 is a perspective view of a complex root canal plugging apparatus for dental work in accordance with the present invention.

FIG. 1 shows a complex root canal plugging apparatus 10 of the present invention. The apparatus 10 includes a gun 12 for heating and injecting filler material such as Gutta Percha, a pen 14 for compacting the filler material, and a controller 16 for controlling the operation of the gun 12 and the pen 14. The controller 16 includes a selection switch 18, a mode switch 20, mode display lamps 22, a display window 24, a temperature setting switch 26, and a gun temperature setting switch 28. The selection switch 18 controls either the pen 14 or the gun 12, or both simultaneously. The mode switch 20 controls electric current for adjusting the amount of electric current for four different types of pen tips 30, each of which has a different size, and is installed at the pen 14. The mode display lamps 22 display the selected mode. The display window 24 displays temperatures set for the gun 12 and the pen 14.

Figure 2:
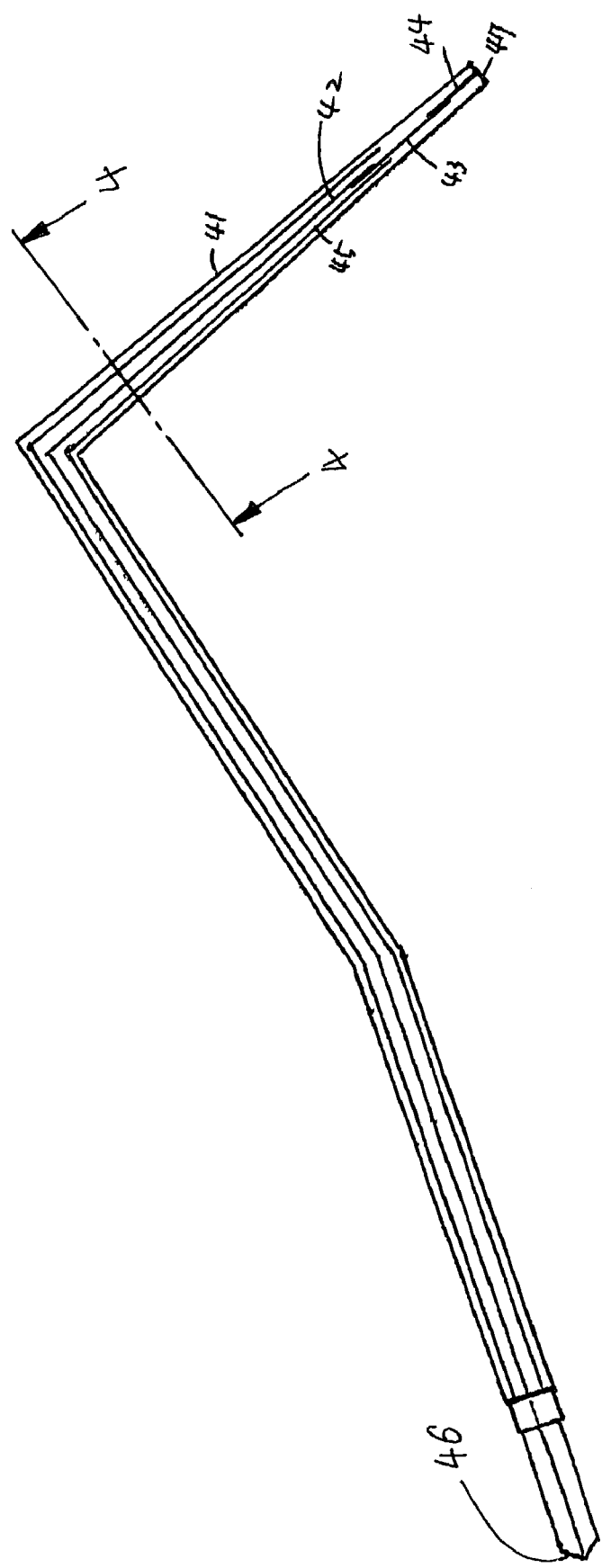
FIG. 2 is a schematic sectional view of a pen tip of the plugging apparatus.
Figure 3:
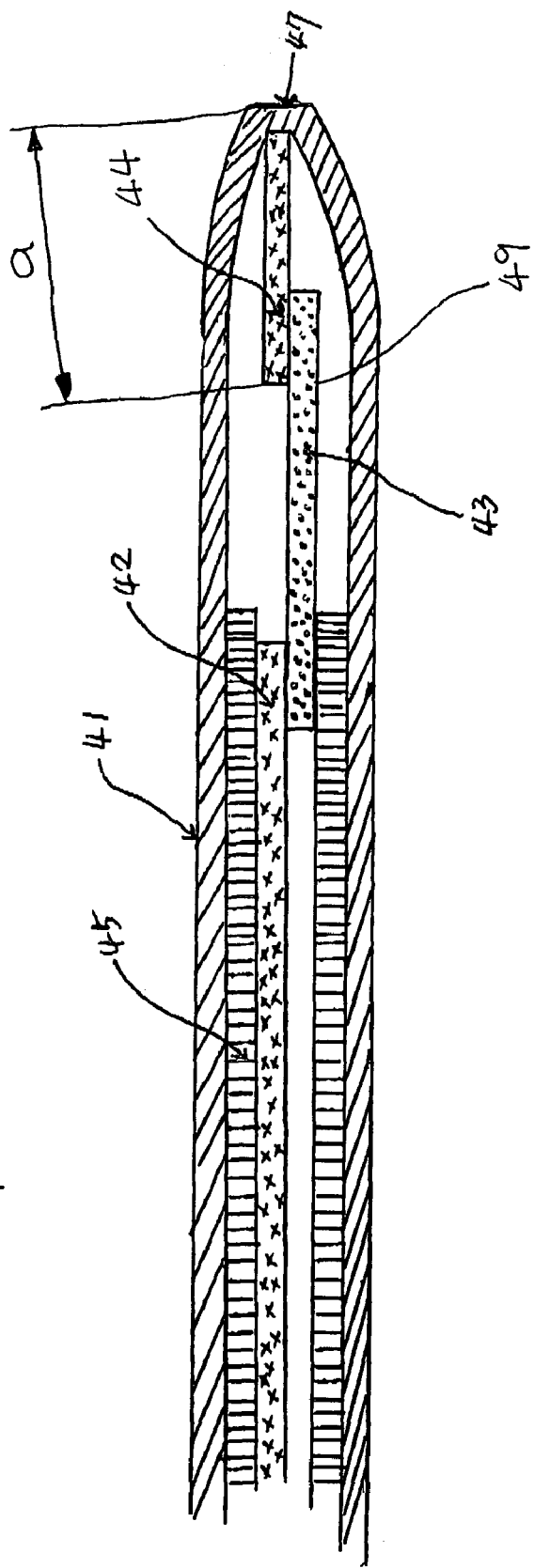
FIG. 3 is an enlarged partial sectional view of the pen tip.
Figure 4:
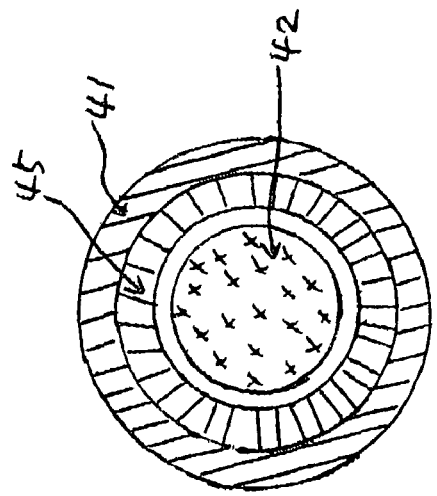
FIG. 4 is a sectional view of the pen tip taken along the line 4—4 of FIG. 2.

The pen 14 holds the pen tip 30. FIGS. 2–4 show the pen tip 30 in detail. The pen tip 30 has a shape adapted to be inserted into the root canal. The pen tip 30 heats the filler material to soften the filler material, and compacts the filler material so that the softened filler material flows into complex shapes of the root canal.

The pen tip 30 is electrically connected to the pen 14. The pen tip 30 has a hollow body 41, a heating element 43, and a temperature sensor 49. The body 41 has a first end 46 and a second end 47. The first end 46 is attached to the pen 14, and the second end 47 is inserted into the root canal when the pen tip 30 is used in dental work. The body 41 of the pen tip 30 is tapered toward the second end.

As shown in FIG. 3, The heating element 43 is positioned inside the body 41 at a predetermined distance a from the second end 47. The predetermined distance a is in a range from about 2 mm to about 3 mm. The distance is measured from the second end 47, and the thickness of the body 41 at the second end is 47 negligible.

The heating element 43 also forms the temperature sensor 49. The temperature sensor 49 measures the temperature at the second end 47.

The pen tip 30 further includes a first conductive wire 42, a second conductive wire 44, and an insulation layer 45. The first conductive wire 42 is electrically connected with the heating element 43 and extends toward the first end 46. The second conductive wire 44 electrically connects the heating element 43 and the second end 47.

The insulation layer 45 insulates the first conductive wire 42 from the body 41 as shown in FIG. 4.

The body 41 is made of stainless steel. The conductive wires 42, 44 are made of silver, which has excellent electric conductivity. The heating element 43 is made of Chromel, which is a Ni—Cr alloy. When the electric current that is transferred though the first conductive wire 42 reaches the heating element 43, in which electric conductivity drops substantially and electric resistance increases substantially, the electric current generates heat. The generated heat is transferred to the second end 47 via the second conductive wire 44. Since heat generation starts at a portion that is 2–3 mm away from the second end 47, damage to tissues including the root canal apex and periodontal membrane is prevented. Such damage was caused by abrupt heat transfer from the pen tip end in the prior art since the tip end was heated directly.

The insulation layer 45 is made of polyimide or Kapton tube, which has good insulation property.

The temperature sensor 49 is a K-type temperature sensor. The thermoelectric voltage at the junction point of the second conductive wire 44 and the heating element 43 is proportional to the temperature at the junction point, and thus at the second end 47. The temperature information of the temperature sensor 49 is sent to the controller 16 thereby making it possible to control the temperature actively and precisely. This is in contrast with a pen tip of prior art, in which a tip end is heated as programmed without sensing the temperature and a large electric current is supplied regardless of the programmed temperature.

Figure 5:
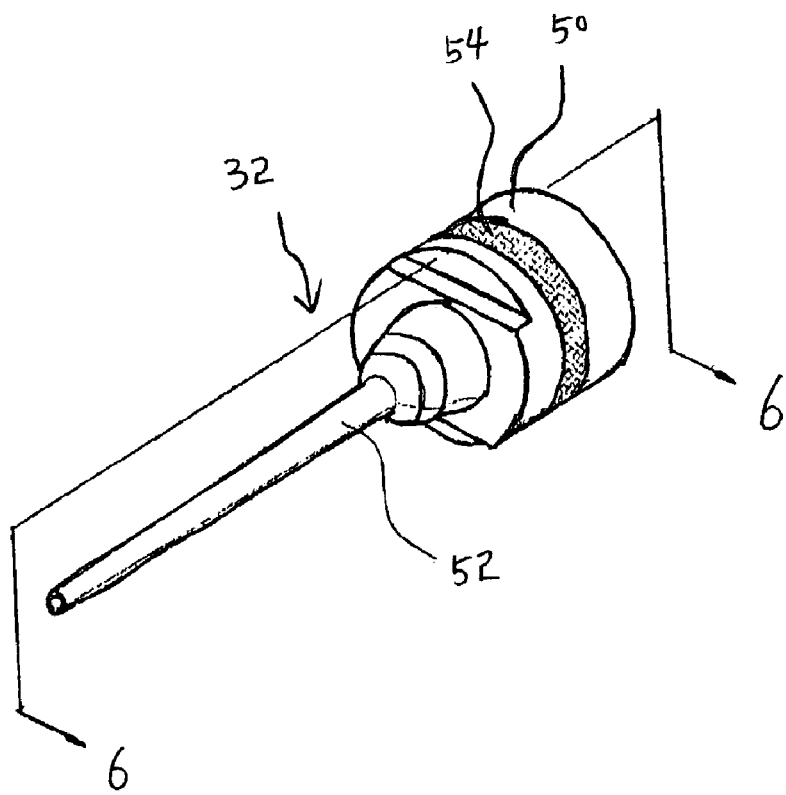
FIG. 5 is a perspective view of a needle.
Figure 6:
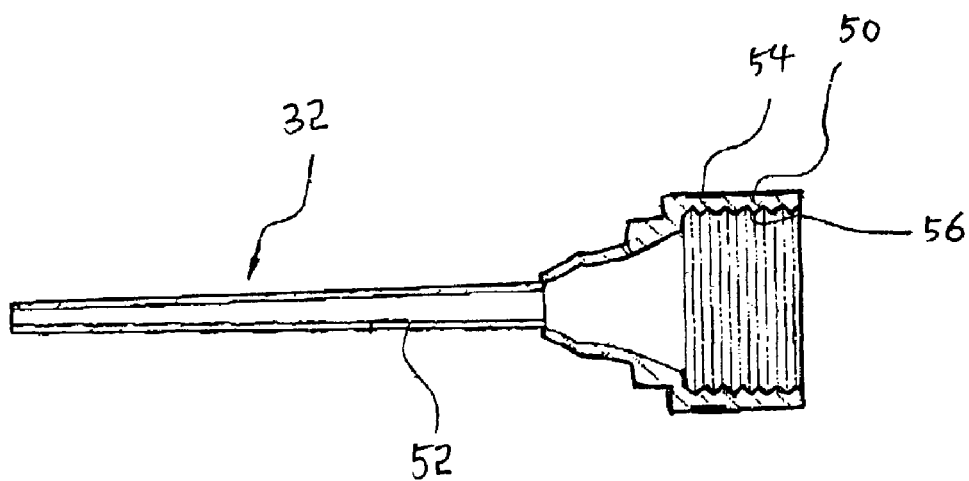
FIG. 6 is a sectional view of the needle taken along the line 6—6 of FIG. 5.

FIGS. 5 and 6 show a needle 32 for injecting the filler material into the root canal. The needle 32 is held by the gun 12. The needle 32 has a cap 50 and a needle portion 52 fixed to the cap 50 by welding, etc. The cap 50 is detachably attached to the gun 12. The cap 50 has a knurled portion 54 on its outer periphery for preventing slipping when a user wearing rubber gloves fits the needle 32 to the gun 12. The needle portion 52 is hollow and has a shape of taper toward its free end. The size of the taper is in a range from about 2/100 to about 6/100. The taper coincides with the taper of the root canal that is formed by a drilling device, so as to prevent flowing off of the filler material between the wall of the root canal and the needle 32, thereby enhancing plugging efficiency. Also, uniform plugging is achieved since the filler material naturally pushes the needle 32 out of the root canal, preventing non-uniform plugging, which might be caused by pulling the needle 32 manually.

The cap 50 has a female-thread portion 56 that engages with a male thread portion (not shown) provided on the gun 12.

General operations with the gun 12 and the pen 14 are shown, for example, in U.S. application Ser. No. 10/279,233 by the applicant, filed on Oct. 25, 2002, the disclosure of which is hereby incorporated by reference.

Figure 7:
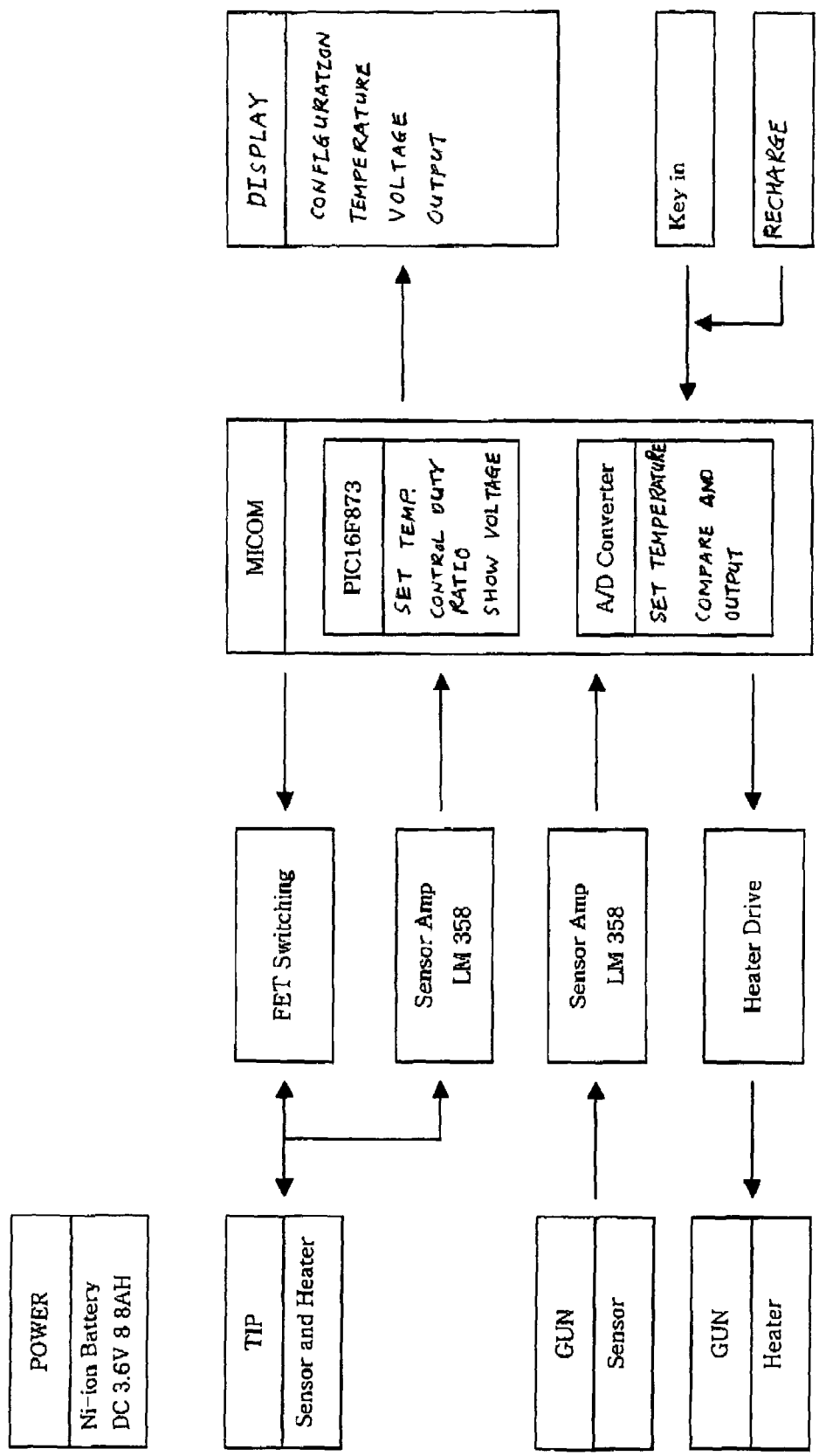
FIG. 7 is a block diagram showing components of the complex root canal plugging device.

FIG. 7 shows blocks that consist the controller 16.

With the above construction, the temperature information of the pen tip is instantly sent to the controller by the K-type sensor to enable precise temperature control so that safe and stable dental cure is obtained. The needle is assembled to the gun with the needle's cap, which is far more convenient than the conventional hub needle. The needle is also resistive to fracture when it is bent or unbent.

The root canal plugging device of the present invention may also be used for applying sealant to a tooth surface that has been eroded by tooth-decay. In the prior art, sealant was inserted into a narrow, elongate groove with a sharp, pointed device, which was not a desirable method. The pen tip of the present invention may be used to heat the sealant to 50 degree Celsius, thereby giving the sealant fluidity.

Although the invention has been described in considerable detail, other versions are possible by converting the aforementioned construction. Therefore, the scope of the invention shall not be limited by the specification specified above.

What is claimed is:

1. A root canal plugging apparatus for dental work, wherein the apparatus plugs a root canal by filling the root canal with a filler material, the apparatus comprising:
   a) a pen tip for compacting the filler material in the root canal;
   b) a pen for holding the pen tip;
wherein the pen tip is electrically connected to the pen, wherein the pen tip has a hollow body, a heating element, and a temperature sensor, wherein the body has a first end and a second end, wherein the first end is attached to the pen, wherein the second end is capable of being inserted into the root canal, wherein the heating element is positioned inside the body in a way that heat is generated at a predetermined distance from the second end, and the temperature sensor is positioned inside the body, wherein the temperature sensor measures the temperature at the second end, wherein the pen tip further includes a first conductive wire, a second conductive wire, and an insulation layer, wherein the first conductive wire is electrically connected with the heating element and extends toward the first end, wherein the second conductive wire electrically connects the heating element and the second end, and wherein the insulation layer insulates the first conductive wire from the body.

2. The apparatus of claim 1, wherein the body is made of stainless steel, wherein the conductive wire is made of silver, wherein the heating element is made of chromel, and wherein the insulation layer is made of polyimide.

3. A root canal plugging apparatus for dental work, wherein the apparatus plugs a root canal by filling the root canal with a filler material, the apparatus comprising:
   a) a pen tip for compacting the filler material in the root canal;
   b) a pen for holding the pen tip;
wherein the pen tip is electrically connected to the pen, wherein the pen tip has a hollow body, a heating element, and a temperature sensor, wherein the body has a first end and a second end, wherein the first end is attached to the pen, wherein the second end is capable of being inserted into the root canal, wherein the heating element is positioned inside the body in a way that heat is generated at a predetermined distance from the second end, and the temperature sensor is positioned inside the body, wherein the temperature sensor measures the temperature at the second end, the apparatus further comprising a needle for injecting the filler material into the root canal, and a gun for holding the needle, wherein the needle has a cap and a needle portion fixed to the cap, wherein the cap is detachably attached to the gun, wherein the pen tip further includes a first conductive wire, a second conductive wire, and an insulation layer, wherein the first conductive wire is electrically connected with the heating element and extends toward the first end, wherein the second conductive wire electrically connects the heating element and the second end, and wherein the insulation layer insulates the first conductive wire from the body.

4. The apparatus of claim 1, wherein the body is made of stainless steel, wherein the conductive wire is made of silver, wherein the heating element is made of chromel, and wherein the insulation layer is made of polyimide.

* * * * *